(12) United States Patent
Yasuda et al.

(10) Patent No.: US 7,173,692 B2
(45) Date of Patent: Feb. 6, 2007

(54) DEVICE AND METHOD FOR OPTICALLY INSPECTING OPERATING HOLES FORMED IN HEADS OF SCREWS

(75) Inventors: Nobuyuki Yasuda, Osaka (JP); Masahiro Togawa, Osaka (JP)

(73) Assignee: Yutaka Co., Ltd., Osaka (JP)

( * ) Notice: Subject to any disclaimer, the term of this patent is extended or adjusted under 35 U.S.C. 154(b) by 234 days.

(21) Appl. No.: 10/837,714

(22) Filed: May 4, 2004

(65) Prior Publication Data

US 2004/0223143 A1 Nov. 11, 2004

(30) Foreign Application Priority Data

May 6, 2003 (JP) .............................. 2003-127940
Feb. 12, 2004 (JP) .............................. 2004-035348

(51) Int. Cl.
*G01N 21/00* (2006.01)
(52) U.S. Cl. ................................. 356/237.1; 356/237.6
(58) Field of Classification Search ...................... None
See application file for complete search history.

(56) References Cited

U.S. PATENT DOCUMENTS

| 5,165,551 | A | * | 11/1992 | Frost ............................ 209/538 |
| 6,346,982 | B1 | * | 2/2002 | Yasuda et al. ............ 356/237.1 |
| 6,474,919 | B2 | * | 11/2002 | Wallace et al. .............. 411/301 |
| 6,620,246 | B2 | * | 9/2003 | Alaimo et al. .............. 118/681 |
| 6,761,126 | B2 | * | 7/2004 | DiMaio et al. .............. 118/306 |
| 2002/0180959 | A1 | * | 12/2002 | Nakajima et al. ......... 356/237.1 |
| 2005/0155915 | A1 | * | 7/2005 | Ong et al. ................... 209/561 |

* cited by examiner

*Primary Examiner*—Michael P. Stafira
(74) *Attorney, Agent, or Firm*—Wenderoth, Lind & Ponack, L.L.P.

(57) ABSTRACT

Image inspection is used to inspect defective or non-defective screw heads. An inspection device includes an inspecting portion for positioning and holding a screw, with a head, with the head up, a CCD camera provided right over the inspecting portion, an annular light source arranged between the inspecting portion and the CCD camera, and a determining device for processing an image of the CCD camera and determining whether the screw is defective or non-defective based on this processed image. An operating hole of the screw is illuminated by the annular light source so that no shadow forms to vividly photograph a hole bottom of the operating hole with the CCD camera. It is also possible to inspect a top surface of a head of a screw.

18 Claims, 5 Drawing Sheets

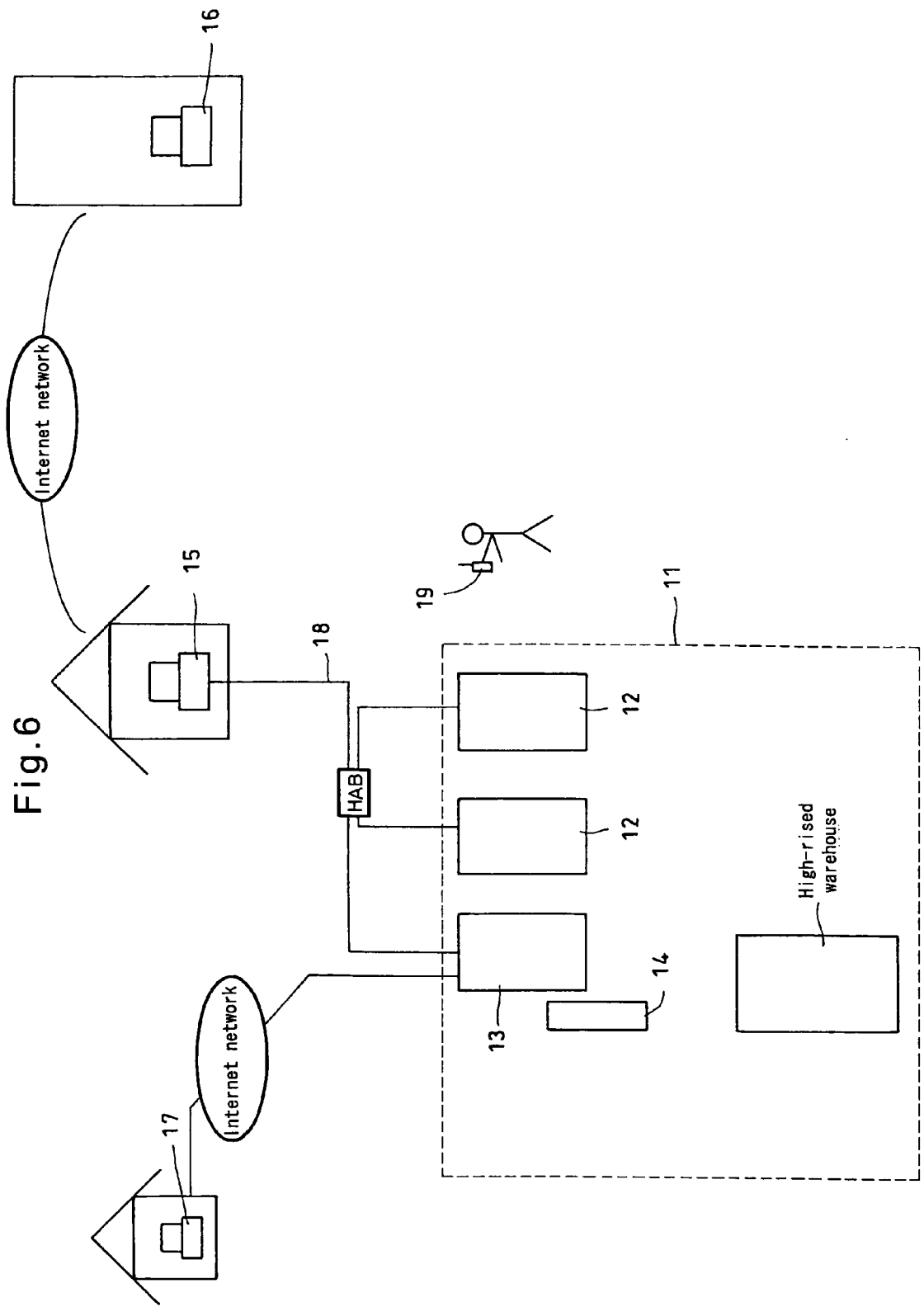

DEVICE AND METHOD FOR OPTICALLY INSPECTING OPERATING HOLES FORMED IN HEADS OF SCREWS

BACKGROUND OF THE INVENTION

This invention relates to an inspection device and method for optically inspecting operating holes formed in heads of screws (among screws having a head referred to in this invention, bolts having an operating hole are included) or the heads' top surfaces, and a method for detecting that chipping has developed in a punch of a header for working the heads of screws by use of the inspection device.

Screws with a head are inspected for necessary items after manufacture and delivered after removing defectives. Among inspection items, there is inspection of operating holes formed in heads of screws. Among operating holes of screws, there are hexagonal, Torx, square, cross, plus-minus, which is a combination of cross and minus, HIOS (trade name) and special-shaped holes.

Operating holes are simultaneously formed when screw heads are formed by a header. If there is minute chipping at a tip of a portion of a punch of the header for forming operating holes, it is transferred to a bottom of a hole, so that the bottom will partially bulge. Further, after working of operating holes by the header has been normally performed, foreign matter produced due e.g. to working of threads may enter the hole and the foreign matter may be fixed to and remain in the bottom of the hole when threads have been plated with the foreign matter stuck to the bottom of the hole. In this case too, the bottom of the hole will bulge.

If such defects develop, an operating bit cannot be properly received in the operating hole, so that there may arise trouble in operation of the screw, or the hole may be crushed due to forcible operation. Thus, inspection of such an operating hole has heretofore been performed by inserting a dummy bit to confirm a depth of such a hole.

Inspection by a dummy bit has a problem in terms of a treating capacity, and a cost is high too. Therefore, we thought of employing an efficient image inspection method. But with a conventional image inspection device, only if inspection areas are limited to central portions of operating holes, is inspection is possible. But it was impossible to inspect more important portions where defects tend to develop.

Defects of operating holes tend to develop not at the central portions of the holes but at outer peripheral portions thereof. For example, since the above-described chipping of the header develops at an outer peripheral edge at the tip of the punch, defects of operating holes due to this chipping naturally develop at the outer peripheral portions of the holes.

If trials are made to inspect the outer peripheral portions of the operating holes, where these defects concentrate, with an existing inspection device, a shaded region is formed at edge portions along an outer periphery of the operating holes, so that it is difficult to see a difference between recesses and protrusions of hole bottoms from images of a camera. Since defects are protrusions, it is necessary to see the recesses and protrusions of the hole bottoms for image inspection. Since this was impossible, there was no other way but to employ an inefficient method of confirming the depth with a dummy bit.

Therefore, an object of this invention is to make it possible to detect defects of operating holes with image inspection to improve inspection efficiency.

SUMMARY OF THE INVENTION

According to this invention, there is provided a method of inspecting screws, having heads, comprising: positioning and holding a screw with its head facing a CCD camera in an inspecting portion; throwing illuminating light from an annular light source, arranged on a side of the inspecting station nearer to the CCD camera to surround a view field of the camera, on the head of the screw; photographing a top of the head of the screw, which is arranged in the inspecting portion with the camera in this state; processing the image obtained; and determining whether an operating hole formed in the head of said screw or a top surface of the head is defective or non-defective based on information after processing. There is also provided an inspection device for screws, having heads, comprising: an inspecting portion for positioning and holding a screw with its head facing a CCD camera; the CCD camera, which opposes the head of the screw that has been held in the inspecting portion; an annular light source arranged between the inspecting portion and the CCD camera to surround a view field of the CCD camera; and a determining device for processing an image of the CCD camera and determining between a defective and non-defective screw based on the processed image, wherein a top of the screw is photographed by the CCD camera while throwing light from the annular light source from an obliquely forward direction on the head of the screw that has been placed in the inspecting portion, and an image obtained is processed to determine in the determining device whether an operating hole formed in the head of the screw or a top surface of the head is defective or non-defective.

There is also provided a method of detecting chipping of a punch of a header for forming heads of screws, wherein inspection of operating holes or top surfaces of screws with heads that are fed from a head forming step is conducted using the above inspection method or inspection device, and if there are defects in inspection areas set on each operating hole or top surface and detection of defects in identical inspection areas have been made continuously for a plurality of screws, determination is made that chipping has developed in the punch of the header.

The inspection device may further comprise: a turntable for receiving screws with heads to be inspected in cutout grooves formed along an outer periphery of the turntable at constant pitches with their heads facing upward, and transporting the screws with the heads that have been received in the cutout grooves to an inspecting portion by turning the turntable with a vertical shaft as a fulcrum; and a dispensing portion for sorting the screws on which determination of heads has been made as to whether the heads are defective or non-defective, into defectives and non-defectives and taking these screws out of the cutout grooves.

The inspection device may further comprise: a turntable having radially extending grooves provided on a top surface of the turntable along its outer periphery at constant pitches to receive screws with heads to be inspected so that the screws are horizontal with their heads on an outer peripheral side to deliver the screws that have been received in the grooves to an inspecting portion by turning the turntable; and a dispensing portion for sorting the screws on which determination of heads has been made as to whether the heads are defective or non-defective, into defectives and non-defectives and taking these screws out of the cutout grooves.

Preferably, the annular light source of the inspection device has its center arranged on a line connecting a center of the inspecting portion and a center of the CCD camera.

BRIEF DESCRIPTION OF THE DRAWINGS

Other features and objects of the present invention will become apparent from the following description made with reference to the accompanying drawings, in which:

FIG. 6 is a view showing an example of a production system for screws with heads;

DETAILED DESCRIPTION OF THE PREFERRED EMBODIMENTS

Figure 1:
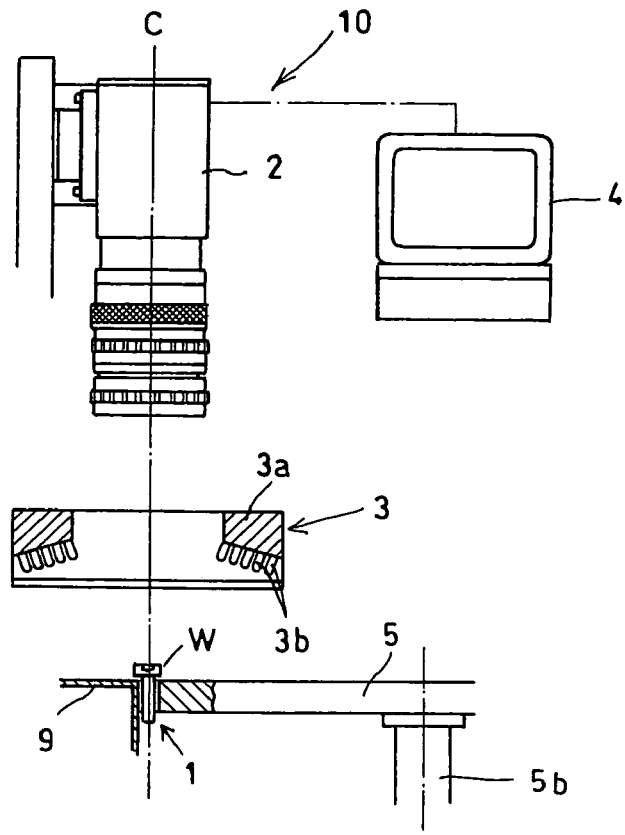
FIG. 1 is an entire schematic view of an inspection device of this invention.
Figure 2:
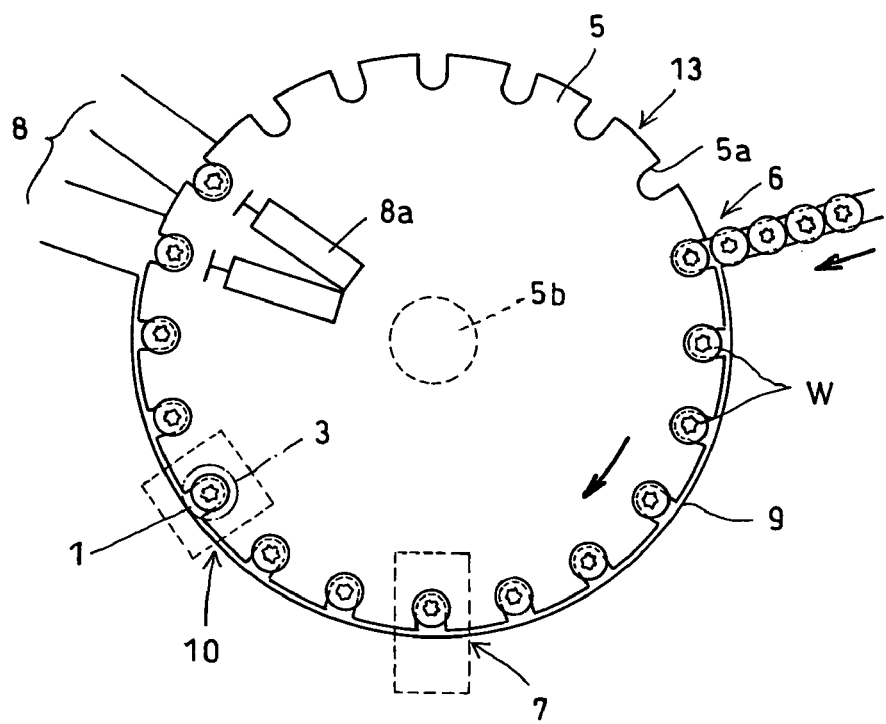
FIG. 2 is a plan view schematically showing a sorter in which the device of FIG. 1 is mounted.

FIGS. 1 and 2 show an embodiment of an inspection device of this invention. The inspection device includes an inspecting portion 1 for positioning and holding a screw W having a head to be inspected, a CCD camera 2 arranged right over the inspecting portion 1, an annular light source 3 arranged between the inspecting portion 1 and the CCD camera 2, and a determining device 4 for performing determination as to defective and non-defective operating holes by processing images photographed by the CCD camera 2. The inspection device 10 comprises these four elements.

The inspection device 10 is mounted in e.g. a sorter 13 of FIG. 2, which uses a turntable 5. In the sorter 13 of FIG. 2, in an outer peripheral portion of the turntable 5, which is rotated with a vertical shaft 5b as a fulcrum, cutout grooves 5a into which shanks of screws W having heads (hereinafter merely mentioned as screws W) are inserted, are formed at regular pitches. At a supply portion 6, screws W are introduced into the cutout grooves 5a. The heads of the screws W are supported on a top surface of the table 5. In this state, the table 5 is turned intermittently or continuously to feed screws W to an inspecting portion 7 for performing inspection of lengths of shanks of the screws, or the inspecting portion 1 for performing inspection as to defective or non-defective operating holes with the inspection device 10 of FIG. 1 (a number of inspecting portions of the sorter can be increased or reduced as necessary).

Screws W that have passed a final inspecting portion are sorted into defectives and non-defectives and taken out of the turntable 5 at a dispensing portion 8. In FIG. 2, 9 is a guide plate for closing inlets of the cutout grooves 5a in a range from the supply portion 6 to the dispensing portion 8 in order to prevent a fall of screws W. A dispensing device at the dispensing portion 8 is not limited to illustrated actuators 8a. It is also possible to dispense the screws by blowing air.

The CCD camera 2 photographs the head of a screw W brought into the inspecting portion 1 from directly above the head.

Further, the illustrated annular light source 3 is formed by providing numerous light emitting diodes (LEDs) 3b on an underside of a ring 3a. If the annular light source 3 has its center placed on or near a line connecting a center of the inspecting portion 1 and a center of the CCD camera 2, it is possible to uniformly throw light on the inspecting portion 1 from all areas in a circumferential direction.

Figure 3B:
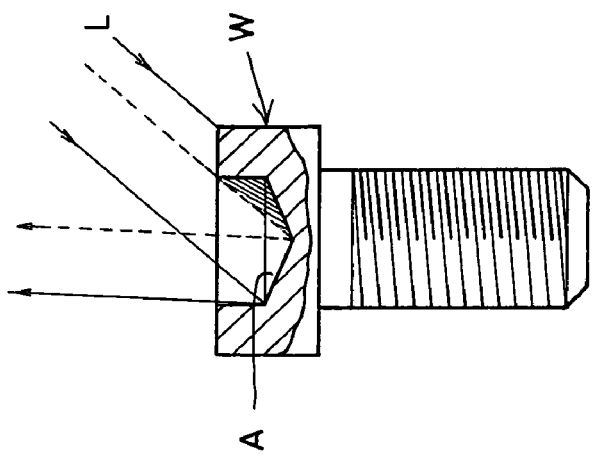
FIG. 3B is a view showing an illuminating state of an operating hole on an enlarged scale.
Figure 3A:
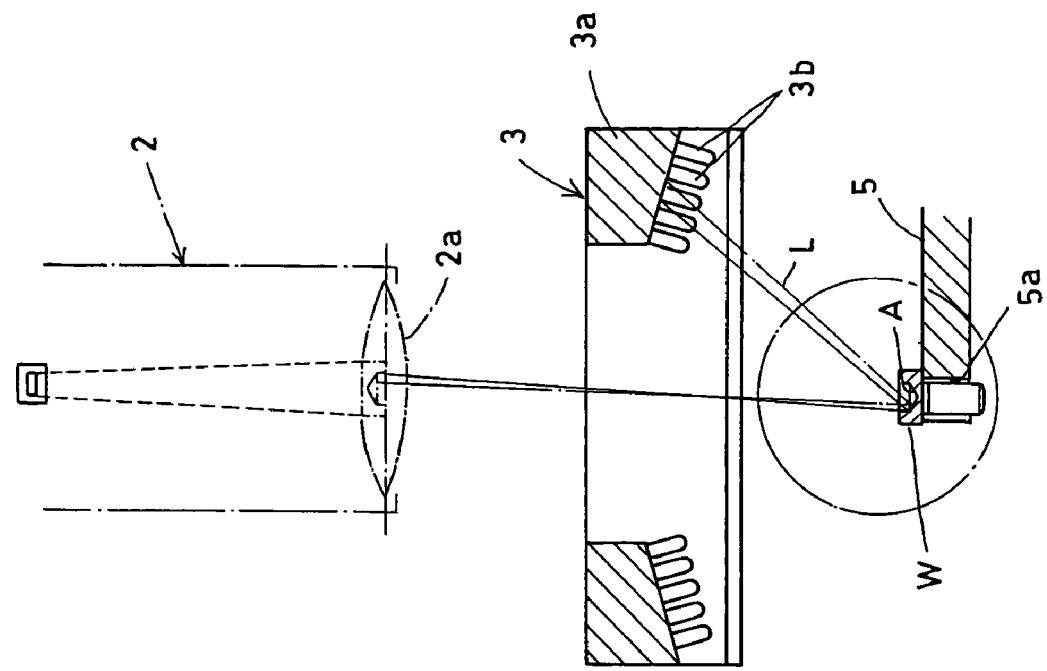
FIG. 3A is an explanatory view of an illuminating principle by the inspection device of this invention.

FIGS. 3A and 3B schematically show how illuminating light L is thrown on the head of a screw W placed in the inspecting portion 1 from the annular light source 3. 2a in FIG. 3A shows a lens of the CCD camera 2. In a case of illumination using a point light source, depending on a depth of an operating hole A formed in the head of a screw W or a light projecting angle, there are portions where illuminating light L is interrupted by an edge of the operating hole A and does not reach a hole bottom (hatched portion in FIG. 3B), so that a shadow forms at this portion. But by using the annular light source, the portion where the shadow forms is illuminated brightly by light from an opposite direction, so that no shadow forms. Thus, the hole bottom vividly appears on the camera image. Further, since the illuminating light is thrown obliquely relative to the hole bottom from above, if there are defects (protrusions) on the hole bottom, shadows due to the defects will form there.

Figure 4A:
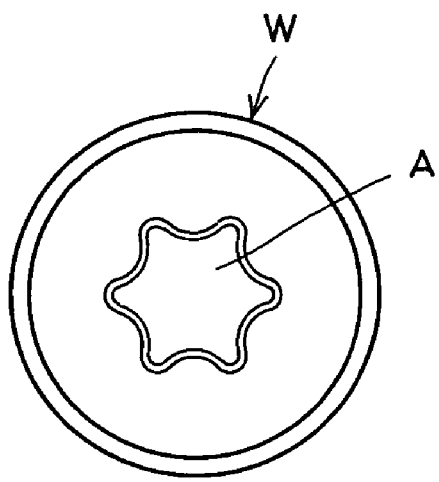
FIG. 4A is a view showing an image of a normal operating hole captured by a CCD camera.
Figure 4B:
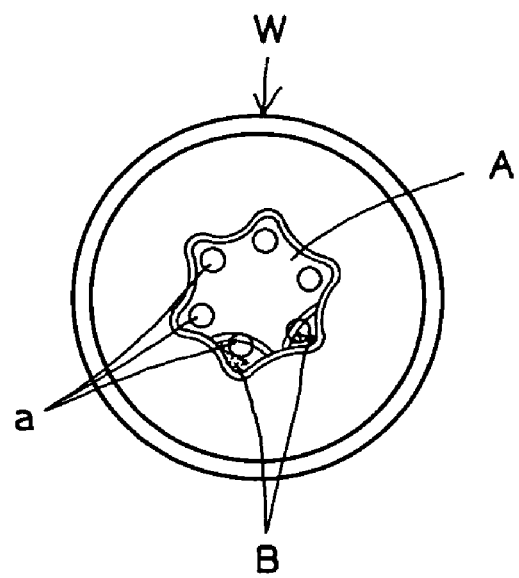
FIG. 4B is a view showing an image of an abnormal operating hole captured by the CCD camera.

FIG. 4A shows an image of a normal operating hole A captured by the CCD camera 2. FIG. 4B shows an image of an operating hole A in which chipping has developed on a punch of a header, and defects B due to the chipping have developed on a hole bottom. The defects B that have appeared on the image of FIG. 4B are displaced to an outer peripheral side of the operating hole A, so that recesses and protrusions are formed. To a position of the defects B, while light emitted from a side where there are the defects B scarcely reaches, light from the other side reaches without being interrupted. Thus, shadows that are not seen on the image of a normal operating hole form at portions where defects have developed. Thus, according to existence or non-existence of such shadows, it is possible to determine whether the hole bottom is defective or non-defective, i.e. whether the operating hole A is defective or non-defective.

The determining device 4 has an image processing portion for subjecting images photographed by the CCD camera 2 to finalizing processing. Further, the determining device 4 has functions of setting inspection areas a enclosed in circles in FIG. 4B, and a function of determining whether the inspection areas a have any defects from processed images.

Figure 5A:
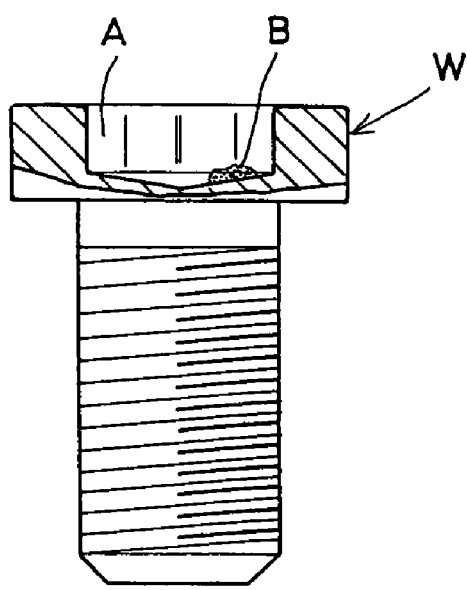
FIG. 5A is a side view showing a Torx screw with its head cut away.
Figure 5B:
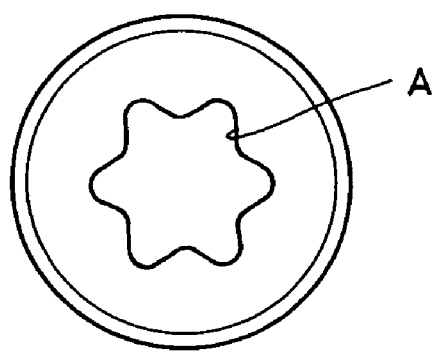
FIG. 5B is a plan view of the head of the Torx screw.

The operating hole A shown in FIG. 3 is an operating hole of a Torx screw shown in FIGS. 5A and 5B and has six grooves with which protrusions of an operating bit engage. Possibility is high that defects of the operating hole A develop at groove portions. Thus, by setting inspection areas at positions enclosed in the circles in FIG. 4B, it is possible to reliably find such defects and reject them.

With the inspection device of this invention, it is possible to perform determination of a defective or non-defective operating hole formed in the head of a screw by image inspection as described above, and thus it is possible to markedly improve inspection efficiency. For example, in continuous inspection using the sorter of FIG. 2, compared with manual operation performed using a dummy bit, a number of screws processed was about three times for Torx screws and about six times for cross screws.

Further, if the inspection device of this invention is arranged in a manufacturing line for screws with heads for determination of defective or non-defective operating holes at heads of screws delivered one after another from a head forming step, it is possible to quickly find that chipping has developed on a punch of the header for forming heads of screws.

Since the punch of the header controls a stroke, it is possible to find a large chipping accompanying change in stroke. But minute chipping that will not influence the stroke cannot be confirmed while the header is operating. If the header is operated at a high speed until such confirmation is made, defectives will be produced in large amounts, which is not preferable.

Thus, the inspection device of this invention is used. If there are defects in inspection areas set for each operating hole, and defects are detected for a plurality of screws at the same inspection area, one can presume that chipping has developed in the header punch. Thus, by this method, it is possible to find chipping early. To screws immediately after working heads thereof with a header, machining oil is stuck. Thus, if image inspection of operating holes is performed with the device of this invention immediately after passing the header, inspection is preferably performed after blowing out machining oil and foreign matter stuck on a hole bottom, by using e.g. air.

FIG. 6 shows an example of a production control system for screws with heads. The production control system includes manufacturing devices 12 for screws with heads that is installed in a manufacturing plant, a sorter 13 of products including the inspection device of this invention, a packaging belt conveyor 14, a personal computer 15 provided in an office of the manufacturing plant, a personal computer 16 provided in a head office of a manufacturer, and a personal computer 17 for controlling the sorter in a company for performing maintenance of the sorter 13.

The manufacturing devices 12 cut materials to a predetermined length, form heads with a header, and form threads. Also, the sorter 13 performs inspection for screws with a head and sorts them into defectives and non-defectives.

The manufacturing devices 12 and the sorter 13 are connected to the personal computer 15 through an LAN network 18 in the company. Further, the personal computers 15 and 16 are adapted to exchange information through the Internet network. By the personal computers 15 and 16, a production state, stock state and the like are comprehensively controlled. Further, salesmen can access the personal computer at the head office using notebook personal computers or PDAs to know the production state and stock state.

In such a production system, it is possible to quickly detect chipping of a punch of a header from defects developed in operating holes of screws produced. It is also possible to detect any other trouble such as stoppage of the device. Thus, it is possible to notify a device operator of the trouble through e.g. cell phone 19.

Here, description was made using a Torx screw as an example. But the device of this invention can be used for inspection of screws having hexagonal, square, cross, plus-minus, HIOS, and special-shaped holes, and inspection of a top surface of the head of a screw. Screws of which the heads are to be inspected may or may not have operating holes.

Inspection of screws may be performed after plating.

Figure 7A:
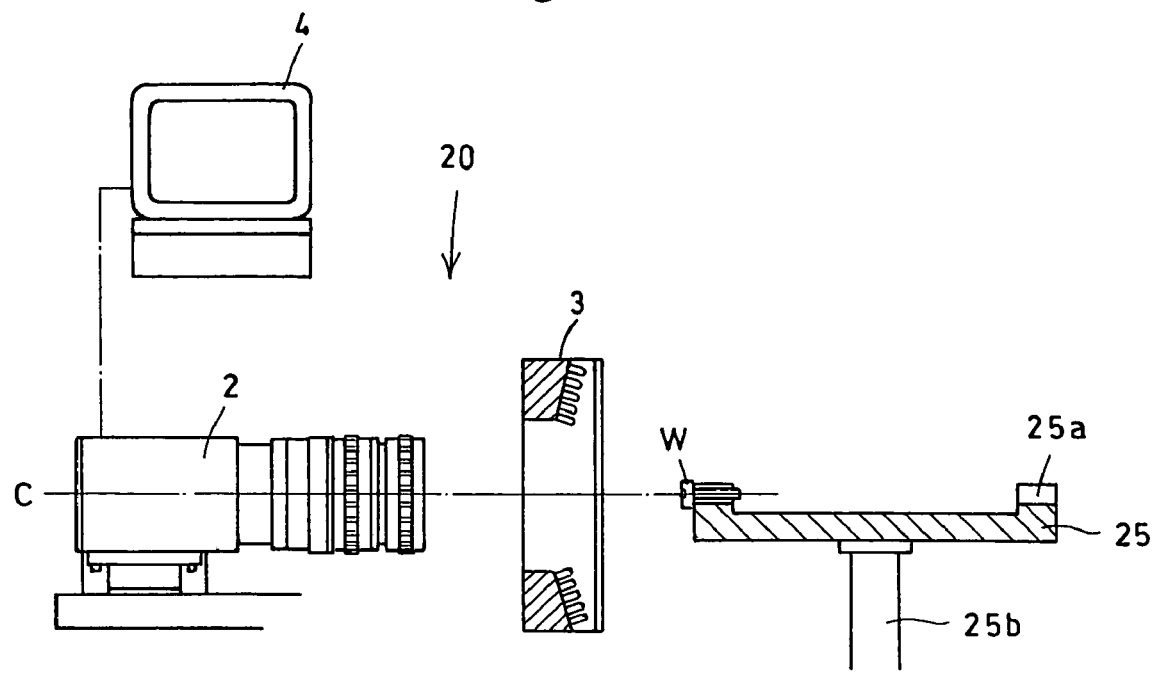
FIG. 7A is an entire schematic sectional view of another embodiment of the inspection device.
Figure 7B:
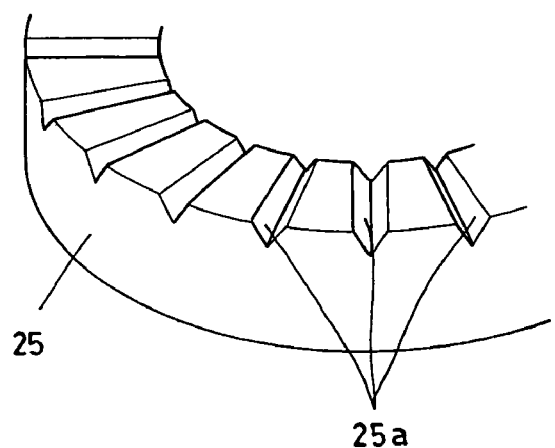
FIG. 7B is a perspective view of grooves formed in a turntable.

Further, the inspection of screws can be performed with screws W to be inspected held horizontally as shown in FIG. 7A. The inspection device of FIG. 7A has a turntable 25 having radially extending grooves 25a provided at an outer peripheral portion of a top surface of the turntable at constant pitches in a circumferential direction. The grooves 25a are preferably V-grooves as shown.

Screws W to be inspected are dropped into the grooves 25a on the top surface of the turntable 25 so as to be horizontal and with their heads on an outer peripheral side. Then, by turning the turntable 25 with a vertical shaft 25b as a fulcrum, the screws W held by the turntable 25 are fed into inspecting portion 1.

The inspecting portion 1, CCD camera 2, which faces the head of a screw W, and annular light source 3, which is arranged between the CCD camera 2 and the turntable 25, are arranged on a horizontal centerline C. In this device too, inspection can be performed in the same manner as with the inspection device of FIG. 2.

A carrier device for screws for inspection with screws W horizontal is not limited to the illustrated turntable 25. For example, parallelly arranged V-grooves or the like may be formed on a carrier surface of an endless transportation path of a conveyor device as represented by a belt conveyor, and screws may be held in the grooves for inspection of the heads of the screws during transportation.

In the inspection device and inspection method of this invention, the annular light source is arranged between the inspecting portion and the CCD camera, and illumination of the head of a screw, with the head arranged in the inspecting portion, is performed with illuminating light from the annular light source. By using the annular light source, since light is thrown on a portion shaded by illumination of a point light source from an opposite side, no shadow forms at an edge portion on an outer periphery of an operating hole.

Further, since the illuminating light from the annular light source is introduced obliquely into the operating hole, if there is any deficiency in the form of a protrusion, a shadow due to the protrusion forms, so that recesses and protrusions on a hole bottom appear vividly on camera images. Thus, it is possible to conduct image inspection of operating holes, which dramatically improves inspection efficiency.

The inspection device of this invention can also be used for inspection as to whether a top surface of a head of a screw is defective or non-defective. Further, by using the inspection method or inspection device of this invention, chipping that has developed in a punch of a header for forming heads of screws can be found quickly based on an inspection state of operating holes or top surfaces of heads.

What is claimed is:

1. A method of inspecting a screw having a head, comprising:
    positioning and holding a screw in an inspecting portion such that a head of said screw faces a CCD camera;
    using an annular light source, arranged between said inspecting portion and said CCD camera so as to surround a view field of said CCD camera, to illuminate at one time an entire inspection area of said head;
    using said CCD camera to photograph said entire inspection area of said head while said entire inspection area is being illuminated by said annular light source, thereby capturing an image of said entire inspection area of said head;
    processing said image; and
    using a determining device to determine whether an operating hole formed in said head, or a top surface of said head, is defective or non-defective based on said image as processed.

2. The method according to claim 1, wherein
    using said annular light source to illuminate said entire inspection area of said head comprises using said annular light source to illuminate said entire inspection area of said head from an oblique direction.

3. The method according to claim 2, further comprising:
holding screws in cutout grooves positioned along an outer periphery of a turntable at constant pitches such that heads of said screws face upward;
transporting said screws to said inspecting portion by rotating said turntable about a vertical axis;
using said annular light source to illuminate at one time an entire inspection area of the head of each of said screws while said each of said screws is at said inspecting portion;
using said CCD camera to photograph said entire inspection area of said head of said each of said screws while said entire inspection area is being illuminated by said annular light source, thereby capturing an image of said entire inspection area of said head of said each of said screws;
processing said image of said entire inspection area of said head of said each of said screws;
determining whether an operating hole formed in said head of said each of said screws, or a top surface of said head of said each of said screws, is defective or non-defective based on said image as processed; and
at a dispensing portion, sorting said screws as defectives or non-defectives based upon a determination as to whether an operating hole formed in a respective said head, or a top surface of a respective said head, is defective or non-defective, and removing said screws from said cutout grooves,
wherein said screw is one of said screws.

4. The method according to claim 2, further comprising:
holding screws in grooves provided in a top surface and along an outer periphery of a turntable at constant pitches, such that said screws are held a horizontal orientation with heads thereof facing radially outwardly;
transporting said screws to said inspecting portion by rotating said turntable;
using said annular light source to illuminate at one time an entire inspection area of the head of each of said screws while said each of said screws is at said inspecting portion;
using said CCD camera to photograph said entire inspection area of said head of said each of said screws while said entire inspection area is being illuminated by said annular light source, thereby capturing an image of said entire inspection area of said head of said each of said screws;
processing said image of said entire inspection area of said head of said each of said screws;
determining whether an operating hole formed in said head of said each of said screws, or a top surface of said head of said each of said screws, is defective or non-defective based on said image as processed; and
at a dispensing portion, sorting said screws as defectives or non-defectives based upon a determination as to whether an operating hole formed in a respective said head, or a top surface of a respective said head, is defective or non-defective, and removing said screws from said grooves,
wherein said screw is one of said screws.

5. The method according to claim 1, further comprising:
holding screws in cutout grooves positioned along an outer periphery of a turntable at constant pitches such that heads of said screws face upward;
transporting said screws to said inspecting portion by rotating said turntable about a vertical axis;
using said annular light source to illuminate at one time an entire inspection area of the head of each of said screws while said each of said screws is at said inspecting portion;
using said CCD camera to photograph said entire inspection area of said head of said each of said screws while said entire inspection area is being illuminated by said annular light source, thereby capturing an image of said entire inspection area of said head of said each of said screws;
processing said image of said entire inspection area of said head of said each of said screws;
determining whether an operating hole formed in said head of said each of said screws, or a top surface of said head of said each of said screws, is defective or non-defective based on said image as processed; and
at a dispensing portion, sorting said screws as defectives or non-defectives based upon a determination as to whether an operating hole formed in a respective said head, or a top surface of a respective said head, is defective or non-defective, and removing said screws from said cutout grooves,
wherein said screw is one of said screws.

6. The method according to claim 1, further comprising:
holding screws in grooves provided in a top surface and along an outer periphery of a turntable at constant pitches, such that said screws are held a horizontal orientation with heads thereof facing radially outwardly;
transporting said screws to said inspecting portion by rotating said turntable;
using said annular light source to illuminate at one time an entire inspection area of the head of each of said screws while said each of said screws is at said inspecting portion;
using said CCD camera to photograph said entire inspection area of said head of said each of said screws while said entire inspection area is being illuminated by said annular light source, thereby capturing an image of said entire inspection area of said head of said each of said screws;
processing said image of said entire inspection area of said head of said each of said screws;
determining whether an operating hole formed in said head of said each of said screws, or a top surface of said head of said each of said screws, is defective or non-defective based on said image as processed; and
at a dispensing portion, sorting said screws as defectives or non-defectives based upon a determination as to whether an operating hole formed in a respective said head, or a top surface of a respective said head, is defective or non-defective, and removing said screws from said grooves,
wherein said screw is one of said screws.

7. An inspection device for inspecting a screw having a head, comprising:
a CCD camera;
an inspecting portion for positioning and holding a screw such that a head of the screw faces said CCD camera;
an annular light source, arranged between said inspecting portion and said CCD camera so as to surround a view field of said CCD camera, for illuminating at one time an entire inspection area of the head; and
a determining device,
wherein said CCD camera is to photograph the entire inspection area of the head while the entire inspection area is being illuminated by said annular light source, to thereby capture an image of the entire inspection area of the head, and said determining device is for processing the image and determining whether an operating hole formed in the head, or a top surface of the head, is defective or non-defective based on the image as processed.

8. The inspection device according to claim 7, wherein said annular light source is for illuminating the entire inspection area of the head from an oblique direction.

9. The inspection device according to claim 8, further comprising:
a turntable having cutout grooves, positioned along an outer periphery of said turntable at constant pitches, for holding the screw and additional screws such that the head of the screw and heads of the additional screws face upward, with said turntable being for transporting the screw and the additional screws to said inspecting portion by rotating said turntable about a vertical axis; and
a dispensing portion for sorting the screw and the additional screws as defectives or non-defectives based upon a determination as to whether an operating hole formed in a respective head, or a top surface of a respective head, is defective or non-defective, and for removing the screw and the additional screws from said cutout grooves.

10. A method of detecting chipping of a punch of a header used for forming heads of screws, comprising:
using the inspection device of claim 9 to determine whether operating holes or top surfaces of screws, fed from a head forming operation, have defects; and
if said holes or top surfaces have defects in identical inspection areas for sequential ones of said screws, determining that chipping has developed in the punch of the header.

11. The inspection device according to claim 8, further comprising:
a turntable having radially extending grooves, provided on a top surface and along an outer periphery of said turntable at constant pitches, for holding the screw and additional screws in a horizontal orientation such that the head of the screw and heads of the additional screws face radially outwardly, with said turntable being for transporting the screw and the additional screws to said inspecting portion by rotating said turntable; and
a dispensing portion for sorting the screw and the additional screws as defectives or non-defectives based upon a determination as to whether an operating hole formed in a respective head, or a top surface of a respective head, is defective or non-defective, and for removing the screw and the additional screws from said grooves.

12. A method of detecting chipping of a punch of a header used for forming heads of screws, comprising:
using the inspection device of claim 11 to determine whether operating holes or top surfaces of screws, fed from a head forming operation, have defects; and
if said holes or top surfaces have defects in identical inspection areas for sequential ones of said screws, determining that chipping has developed in the punch of the header.

13. A method of detecting chipping of a punch of a header used for forming heads of screws, comprising:
using the inspection device of claim 8 to determine whether operating holes or top surfaces of screws, fed from a head forming operation, have defects; and
if said holes or top surfaces have defects in identical inspection areas for sequential ones of said screws, determining that chipping has developed in the punch of the header.

14. The inspection device according to claim 7, further comprising:
a turntable having cutout grooves, positioned along an outer periphery of said turntable at constant pitches, for holding the screw and additional screws such that the head of the screw and heads of the additional screws face upward, with said turntable being for transporting the screw and the additional screws to said inspecting portion by rotating said turntable about a vertical axis; and
a dispensing portion for sorting the screw and the additional screws as defectives or non-defectives based upon a determination as to whether an operating hole formed in a respective head, or a top surface of a respective head, is defective or non-defective, and for removing the screw and the additional screws from said cutout grooves.

15. A method of detecting chipping of a punch of a header used for forming heads of screws, comprising:
using the inspection device of claim 14 to determine whether operating holes or top surfaces of screws, fed from a head forming operation, have defects; and
if said holes or top surfaces have defects in identical inspection areas for sequential ones of said screws, determining that chipping has developed in the punch of the header.

16. The inspection device according to claim 7, further comprising:
a turntable having radially extending grooves, provided on a top surface and along an outer periphery of said turntable at constant pitches, for holding the screw and additional screws in a horizontal orientation such that the head of the screw and heads of the additional screws face radially outwardly, with said turntable being for transporting the screw and the additional screws to said inspecting portion by rotating said turntable; and
a dispensing portion for sorting the screw and the additional screws as defectives or non-defectives based upon a determination as to whether an operating hole formed in a respective head, or a top surface of a respective head, is defective or non-defective, and for removing the screw and the additional screws from said grooves.

17. A method of detecting chipping of a punch of a header used for forming heads of screws, comprising:
using the inspection device of claim 16 to determine whether operating holes or top surfaces of screws, fed from a head forming operation, have defects; and
if said holes or top surfaces have defects in identical inspection areas for sequential ones of said screws, determining that chipping has developed in the punch of the header.

18. A method of detecting chipping of a punch of a header used for forming heads of screws, comprising:
using the inspection device of claim 7 to determine whether operating holes or top surfaces of screws, fed from a head forming operation, have defects; and
if said holes or top surfaces have defects in identical inspection areas for sequential ones of said screws, determining that chipping has developed in the punch of the header.

* * * * *